(12) United States Patent
Li et al.

(10) Patent No.: US 8,586,342 B2
(45) Date of Patent: Nov. 19, 2013

(54) ARTIFICIAL BIOMEMBRANE AND THE METHOD FOR MANUFACTURING THE SAME

(75) Inventors: Qinsheng Li, Wuhan (CN); Yeqin Wang, Wuhan (CN); Ruoxue Wang, Wuhan (CN); Jing Wang, Wuhan (CN)

(73) Assignee: Wuhan Probiotic Spring Biotechnology Co., Ltd., Wuhan (CN)

( * ) Notice: Subject to any disclaimer, the term of this patent is extended or adjusted under 35 U.S.C. 154(b) by 1287 days.

(21) Appl. No.: 12/050,915

(22) Filed: Mar. 18, 2008

(65) Prior Publication Data

US 2008/0160596 A1    Jul. 3, 2008

Related U.S. Application Data

(63) Continuation of application No. PCT/CN2007/002715, filed on Sep. 14, 2007.

(30) Foreign Application Priority Data

Sep. 28, 2006 (CN) .......................... 2006 1 0124636

(51) Int. Cl.
  *C12N 1/00* (2006.01)
(52) U.S. Cl.
  USPC ...................... 435/243; 435/252.4; 435/262.5
(58) Field of Classification Search
  USPC .................................. 435/243, 252.4, 262.5
  See application file for complete search history.

(56) References Cited

U.S. PATENT DOCUMENTS

| 4,659,664 | A | * | 4/1987 | de Buda | 435/176 |
| 5,169,780 | A | * | 12/1992 | Stirling et al. | 435/280 |
| 6,051,411 | A | * | 4/2000 | Turtakovsky et al. | 435/178 |
| 2005/0260704 | A1 | * | 11/2005 | Mahadevan et al. | 435/69.1 |
| 2010/0270228 | A1 | * | 10/2010 | Teichberg | 210/281 |

FOREIGN PATENT DOCUMENTS

CN    1740317 A * 3/2006

OTHER PUBLICATIONS

English translation for CN 1740317 downloaded from the Chinese Patent Office on Mar. 11, 2011, 3 pages.*
Sigma Catalog (1998) p. 237, 262, 371.*

* cited by examiner

*Primary Examiner* — Susan Hanley
(74) *Attorney, Agent, or Firm* — Matthias Scholl P.C.; Matthias Scholl

(57) ABSTRACT

An artificial biomembrane and a method for manufacturing the same. Raw film-forming materials, such as polyvinyl alcohol, sodium alginate and sodium carboxymethyl cellulose, are dissolved in water to form a glue liquid, into which a mixture of coal-based activated carbon powder, diatomaceous earth powder sodium acetate and single strain or multiple strains of microbial cells are added. The resultant glue liquid is immobilized using powder beds or fluidized beds to form artificial biomembranes. The artificial biomembranes can be manufactured in a large-scale, with simple process of immobilization, high efficiency and low cost. The artificial biomembranes can be applied to ecological restorations and different polluted water environments, such as industrial wastewater, sewage, fishing water, landscape water, flowing water and the like.

7 Claims, 2 Drawing Sheets

ARTIFICIAL BIOMEMBRANE AND THE METHOD FOR MANUFACTURING THE SAME

CROSS-REFERENCE TO RELATED APPLICATIONS

This application is a continuation of International Patent Application No. PCT/CN2007/002715 with an international filing date of Sep. 14, 2007, designating the United States, now pending, and further claims priority benefits to Chinese Patent Application No 200610124636.2 filed on Sep. 28, 2006. The contents of these specifications are incorporated herein by reference.

BACKGROUND OF THE INVENTION

1. Field of the Invention

The present invention relates to an artificial biomembrane, especially to an artificial biomembrane for simulating natural biomembranes. The present invention also relates to a method for manufacturing such an artificial biomembrane. These artificial biomembranes are used for ecological restorations and treatments of water environment in pollution.

2. Description of the Related Art

Natural biomembranes in water environment can decompose pollutant and purify water. The results of researches indicate that biomembranes contain thousands and tens of thousands of different kinds of microbes, such as bacteria, fungi, algae, protozoan and the like. They adhere to various substrate surfaces in water environment, and excretive viscous materials are embed to be a structure composed of cells, substrates, interstices, flow channels.

In the filed of sewage treatment, there are activated sludge process and biomembranes process. Microbes are hard core of purification. Natural biological membranes are used in biomembranes process, in which microbes adhere to surfaces of certain carriers in national conditions. There are advantages as follows for this method, 1) no problems of sludge bulking and expedient operation and management;
2) better endurance of changes of sewage quality and quantity;
3) less quantity of residual sludge, reduction of processing cost of sludge and better quality of discharged water.

How can we artificially simulate natural biomembrane and apply? This belongs to the field of immobilized microbe research, that is to immobilize microbial cells of suspended growth on carriers by microbiology and technology to improve processing load and purification efficiency of new enhanced biological treatment technology.

There are a variety of microbial cell immobilization technologies, such as adsorption immobilization, self-immobilization, embedding immobilization and crosslinking immobilization etc. Embedding immobilization is a technology of microbial immobilization on widely research, which can embed and immobilize efficient microbial cells by film-forming polymers to form kindred biomembrane structure for water environment treatment. The advantages are as follows: high concentrations of microbes; in favor of immobilization of dominant Bacteria and improvement of purification efficiency; less yield of sludge; good solid-liquid separation; good resistant capacity of impulse load. However, the technology is still in the laboratory stage in the field of sewage treatment in China. "The technology of immobilized cells sewage treatment is still in the laboratory stage" is cited from "Organic Industrial Wastewater Treatment Theory and Technology" wrote by Jian Yang and the like, Chemical Industry Press 2005. There still exists problems below:

1) complex preparation of immobilized particles, weak mechanical strength, short life;
2) large diffusion resistance, mass transfer capacity to be improved;
3) easy adhesion and float of immobilized particles;
4) large-scale production equipment and technology to be developed.

In order to make immobilized microbial particles, the embedded materials and processes should meet the following requirements:

1) simple process of immobilization and easy large-scale production;
2) low cost;
3) non-deleterious to microbial cells;
4) high density of immobilized cells and joint action of a variety of microbes;
5) good permeability and mass transfer capacity of substrate;
6) good chemical stability and high physical strength;
7) antimicrobial decomposition and long life.

The requirements cited above which the embedded materials and processes should meet are cited from "biological immobilization technology and water pollution control" wrote by Jian-long Wang, the Science Press 2002.

The traditional method of cell immobilization is piercing method, in which the film-forming material containing microbial cells is immobilized by dripping into liquid fixative. For example, sodium alginate is immobilized in $CaCl_2$ solution; polyvinyl alcohol is immobilized in boric acid solution. The process is complex, with long immobilizing and washing time and low preparation efficiency, and difficult to large-scale production.

Microencapsulation is a technology using natural or synthetic polymer materials to embed solid, liquid, even liquid substances to form micro-particles with semipermeable or sealed membrane. The technology solves many technological problems that could not solved by means of traditional technology. The content above is cited from "Food Microcapsule and Ultramicro Pulverization Processing Technology" wrote by Jun Zhang and the like, chemical Industry Press 2004. The technology can be applied to production of artificial biomembranes after amelioration.

So far, the search has not found a published artificial biomembrane for treatment of water environment in pollution and the preparation method.

SUMMARY OF THE INVENTION

Based on above, the object of the present invention is to propose an artificial biomembrane that can be assembled with different strains according to its needs. Furthermore, high cell density and good mass transfer performance, which is not easy to be decomposed and damaged, can be used to in-situ remediation of polluted water, purification of flowing water and sediment treatment of culturing water and water environment. Moreover, good stability and long period of validity are also provided in water environment.

Furthermore, the present invention is intended to specify a new and easy method for manufacturing such artificial biomembranes. The process is to spray film-forming materials containing microbial cells to powder beds or fluidized beds to be immobilized. The method is available to mechanized large-scale production, associated with the characteristic of simple process, high efficiency and low cost.

Technical Measures used in the present invention is detailed below:

1) the beneficial microbe referred in the present invention, which are included in the list of safe strains, are authorized for use in the nation. For example, *Rhodopseudomonas palustris, Bacillus subtilis, Lactobacillus lactis*, L. B. delbruekii, Yeast, *Saccharomyces cererisiae, Aspergillus niger* and the related strains. The concentration of microbial cells is $1\times10^9$-$1\times10^{10}$/ml.

2) the selection range of film-forming materials and composition (W/V) of artificial biomembranes is shown in Table 1:

TABLE 1 the content and film-forming materials of artificial biomembranes

| Material composition | Content |
| --- | --- |
| sodium alginate | 0.1-4 gram |
| polyvinyl alcohol | 0.1-10 gram |
| sodium carboxymethyl cellulose | 0.1-2 gram |
| sodium acetate | 0.5-2 gram |
| coal-based activated carbon powder | 0.1-10 gram |
| diatomaceous earth powder | 0.5-10 gram |
| add water to | 100 ml |

The present invention formula can adjust the stability of artificial biomembranes, and enhance the physical intensity of membrane structure and mass transfer performance, and maintain the high activity of cells. The course of immobilization is easy to operate and shape, and the reduction of adhesion and sedimentation are also easily achieved.

3) The steps for preparing an artificial biomembrane are detailed below:

(1) the applied microbial strains are from large-scale production by manufacturer, with concentrated fermentation liquid, so that cell number can reach $5\times10^{10}$/ml, the microbial strains are single strain or composed of 2-3 kinds of multiple strains, so that the final concentration is $1\times10^{9\text{-}10}$/ml;

(2) add sodium alginate, polyvinyl alcohol and sodium carboxymethyl cellulose into water, heating to 85-90° C. until they are dissolved completely into glue liquid, and cool to room temperature 20-25° C.; mix 100-200 mesh coal-based activated carbon powder, 100-180 mesh diatomaceous earth powder, sodium acetate and concentrated bacterial suspension together, then add the mixture into the glue liquid, at last add water to required volume and mix uniformly;

(3) apply the method for manufacturing microencapsulation with powder beds or fluidized beds to the cell immobilization process of artificial biomembrane, which has been used in food industry, the method for manufacturing microencapsulation is cited from "Food Microcapsule and Ultramicro Pulverization Processing Technology" wrote by Jun Zhang and the like, Chemical Industry Press 2004. Put the glue liquid cited above into the spray device, then press to spray so that fogdrops and microcapsules are free landed on powder beds or fluidized beds, in which silicon dioxide powder, boric acid and gypsum powder are taken as powder beds or fluidized beds for immobilization in the present invention, the ratio of silicon dioxide powder, boric acid powder and gypsum powder is 1-6:0.1-3:0.1-3, fogdrops and microcapsules on powder beds and fluidized beds are immobilized as microcapsule membranes that are then callbacked, the circumfluence and reuse of boric acid powder, silicon dioxide powder and gypsum powder are achieved by vibration screen; this is the innovation of cell immobilization method, this method can also be applied to the preparation of granular and sheet artificial biomembranes.

The step (3) can also be: put the glue liquid cited above in a container in which there are 500 sharp hole pipes on the bottom, the glue liquid dripped on powder beds or fluidized beds through sharp hole pipes with freedom or pressure, silicon dioxide powder, boric acid and gypsum powder taken as powder beds or fluidized beds for immobilization in the present invention, the ratio of silicon dioxide powder, boric acid powder and gypsum powder being 1-6:0.1-3:0.1-3, and separate mineral powder by vibration screen and to get granular membranes.

Compared with existing technologies, the present invention has the following advantages and effects: 1) specific microbial species, safe and nontoxic, high efficiency and density and joint action of different strains; 2) a variety of artificial biomembranes, strong adaptability and wide application range. For example, treatment of eutrophication landscape water and disposal of high concentration of organic wastewater and domestic sewage and the like, especially in-situ remediation of polluted water, purification of flowing water and sediment treatment of culturing water and water environment. 3) stable performance, long period of validity and available reuse. The notable treatment effect has been proved in pilot sewage treatment in Qingyuan of Guangdong province and Beijing Zoo. The former has been more than a year, and the latter has also been five months so far; 4) film-like artificial biomembranes and good mass transfer performance; 5) simple technology and low cost; 6) availability of mechanized processing and large-scale production.

Further exemplary embodiments and advantages of the present invention are explained below by reference to the drawings, in which a depiction to scale and proportion was omitted in order to improve their clarity.

DETAILED DESCRIPTION OF THE INVENTION

Figure 1:
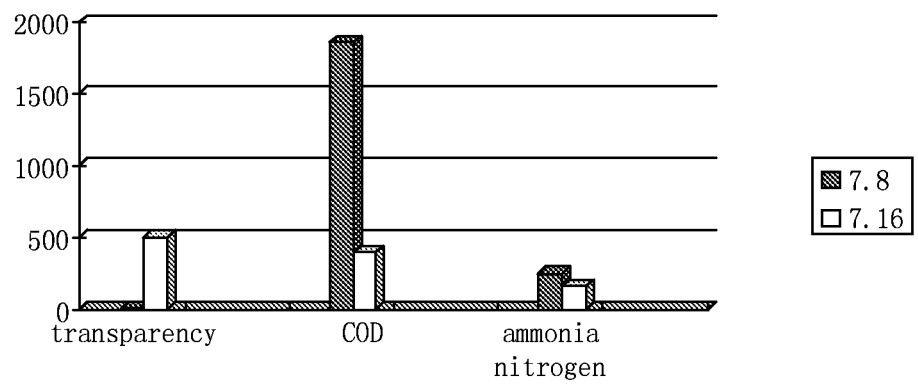
FIG. 1 is a schematic diagram of comparison of water quality of artificial biomembranes before and after treatment.

Table 2 shows the material composition (W/V) of film-forming materials of exemplary embodiments 1-5 in the present invention:

TABLE 2

Material composition (W/V) of film-forming materials of exemplary embodiments 1-5 in the present invention:

| Material | Embodiment 1 | Embodiment 2 | Embodiment 3 | Embodiment 4 | Embodiment 5 |
|---|---|---|---|---|---|
| Microbial cell (/ml) | $5 \times 10^9$ | $1 \times 10^9$ | $1 \times 10^{10}$ | $3 \times 10^9$ | $5 \times 10^9$ |
| sodium carboxymethyl cellulose (gram) | 0.5 | 0.8 | 1 | 2 | 0.1 |
| sodium alginate (gram) | 0.1 | 4 | 0.1 | 2 | 1 |
| polyvinyl alcohol (gram) | 10 | 0.1 | 7.5 | 2.5 | 5 |
| sodium acetate (gram) | 0.5 | 2 | 1 | 0.8 | 0.5 |
| coal-based activated carbon powder (gram) | 0.2 | 10 | 1 | 2 | 0.1 |
| diatomaceous earth powder (gram) | 3 | 1 | 5 | 7.5 | 10 |
| add water to (ml) | 100 | 100 | 100 | 100 | 100 |

The steps of manufacturing an artificial biomembrane are:
1) the applied microbial strains are obtained from large-scale production by manufacturer, associated with concentration after fermentation, so that cell number can reach $5 \times 10^{10}$/ml, the microbial strains being single strain or composed of 2-3 kinds of multiple strains, and the final concentration of microbial cells bought from the market are shown as Table 2, in which microbial cells can choose by themselves a beneficial microbial strain;
2) add sodium alginate, polyvinyl alcohol and sodium carboxymethyl cellulose into water in which the amount of them are described as Table 2, heating to 85-90° C. until they are dissolved completely into glue liquid, and cool to room temperature 20-25° C.; mix 100-200 mesh coal-based activated carbon powder, 100-180 mesh diatomaceous earth powder, sodium acetate and concentrated bacterial suspension together in which the amount of them are described as table 2, then add the mixture into the glue liquid, at last add water to required volume and mix uniformly;
3) put the glue liquid of step 2) into the spray device, then press to spray so that fogdrops and microcapsules are free landed on powder beds or fluidized beds, in which there are silicon dioxide powder, boric acid and gypsum powder on powder beds or fluidized beds, the weight ratio of silicon dioxide powder, boric acid powder and gypsum powder is 3:2:1, fogdrops and microcapsules on powder beds and fluidized beds are immobilized as microcapsule membranes that are then callbacked, the circumfluence and reuse of boric acid powder, silicon dioxide powder and gypsum powder are achieved by vibration screen;

The step (3) can also be: put the glue liquid of step 2) in a container in which there are 500 sharp hole pipes on the bottom, the glue liquid dripped on powder beds or fluidized beds through sharp hole pipes with freedom or pressure, silicon dioxide powder, boric acid and gypsum powder being on powder beds or fluidized beds, the weight ratio of silicon dioxide powder, boric acid powder and gypsum powder is 3:2:1, then separate mineral powder by vibration screen and then to get granular membranes.

Effects of Exemplary Embodiments 1) treatment effect of water in serious pollution: Damuzhou pond has received a lot of waste water from a pharmaceutical factory, the depth of sediments being more than one meter, so that the water become black, smelly and lose the function of drink, use and landscape, which has seriously disturb the production and life of neighborhood.

Figure 2:
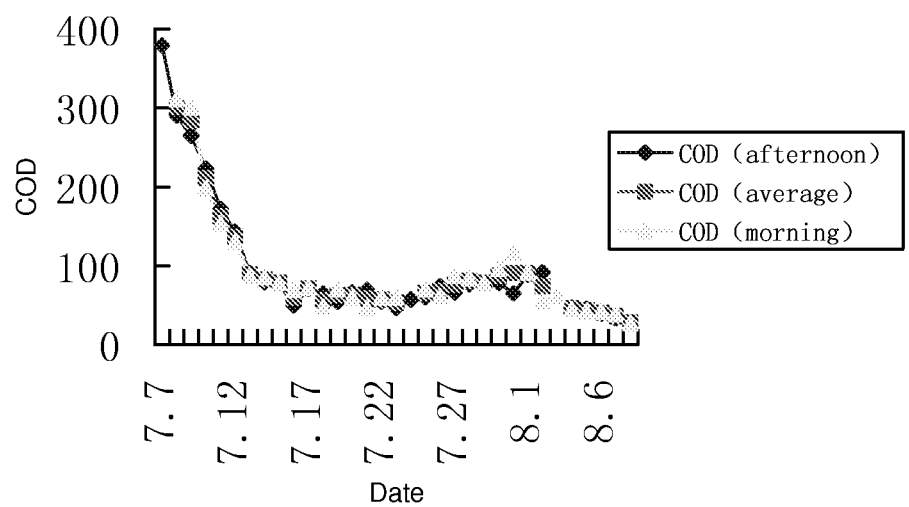
FIG. 2 is a schematic diagram of COD dynamic change of an artificial biomembrane in test pools on July seventh-August eighth 2005.

The pilot location of the artificial biomembrane according to the present invention was in a special plastic enclosure outside of an environmental protection station of a pharmaceutical factory. On the third day of test, the color and quality of water in the enclosure had been obviously improved. The COD of water sample decreased by more than 50%; on the fifth day, the transparency increased to 50 cm, and the COD of the mixture of mud and water reached 78.4%; on the eighth day, the color of water in the enclosure changed from black to clear and ammonia nitrogen decreased by 40%; the water quality will be obviously improved with the existence of sha Chong and paramecium as shown in FIG. 1 and FIG. 2. Two weeks later, 63% of artificial biomembrane sheets in test pool were moved to control pool, and continued COD observation of test pool and control pool. The detection data showed that COD in test pool remained at low level and the total removal ratio of COD and ammonia nitrogen was respectively 92.9% and 83.2%; COD in control pool declined to less than 30.0 mg/l and removal ratio was about 98%. Moreover, ammonia nitrogen declined obviously and water became clear, with almost no sediment. The effect lasted for more than one year without any other measure, which had proved the characteristics of artificial biomembranes, such as extremely good performance, long-term efficiency, available maintenance in less amount and repeated use. The processing efficiency exceeded previous methods.

2) treatment effect of eutrophication landscape water in Beijing zoo: Beijing zoo is a domestic and foreign prestigious popular science corner and tourist attraction. The area of landscape water in the zoo is about 6 hectares. The water is derived from eutrophic long river, associated with animal feed, excreta and the activities of visitors, so that the water is serious eutrophication which influence the landscape and reduces the quality of surrounding environment. Though a variety of domestic and foreign technologies and products have been used for treatment, desired results are not achieved. Therefore, matching technologies and products of artificial biomembranes according to the present invention were on a water treatment experiment in the isolated canal of orangutan house of the zoo from the end of April 2006. The water of experimental zone became clear in a relatively short time, and remained so far. Accordingly, the treatment objectives, which were the increase of transparency, the control of algal blooms, and the removal of odor, in the experimental zone were achieved, which had proved the application effects of products and technologies. It was specified in "decontamination expert—artificial biomembrane" program of "light of science" column on CCTV, first shown on Aug. 29, 2006.

Figure 3:
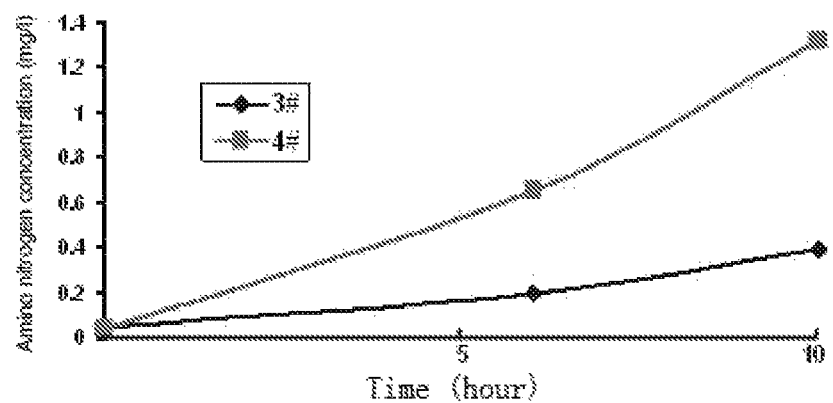
FIG. 3 is a schematic diagram of change of nitrite in test pools compared with shrimp ponds.
Figure 4:
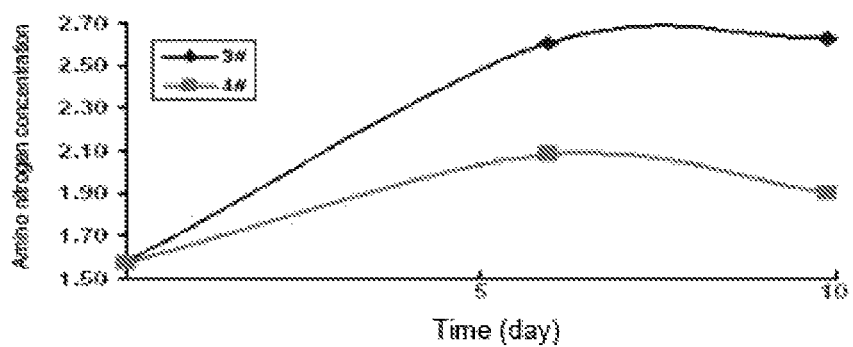
FIG. 4 is a schematic diagram of change of ammonia nitrogen in test pools compared with shrimp ponds.

3) purification effect of culturing water: products of artificial biomembranes according to the present invention are widely applied in the culturing water. The effect is good because ammonia nitrogen and nitrite nitrogen decline obviously in the fish and shrimp ponds, which can effectively reduce culture risk and purify culture environment. As shown in Table 3 and FIG. 3 and FIG. 4.

TABLE 3 concentration change of $NO_2$—N in shrimp ponds

| Date | Control pool | Test pool (1) | Test pool (2) |
|---|---|---|---|
| 09-11 | 0.490 | 0.480 | 0.560 |
| 09-12 | 0.550 | 0.290 | 0.320 |
| 09-13 | 0.320 | 0.270 | 0.250 |
| 09-14 | 0.295 | 0.260 | 0.195 |
| 09-15 | 0.260 | 0.220 | 0.141 |
| 09-16 | 0.149 | 0.107 | 0.066 |
| 09-17 | 0.185 | 0.100 | 0.056 |
| 09-18 | 0.175 | 0.052 | 0.033 |

What is claimed is:

1. An intermediate composition for producing an artificial biomembrane, each 100 ml of the intermediate composition comprising:

| | |
|---|---|
| microbial cell | $1 \times 10^9 - 1 \times 10^{12}$ |
| sodium carboxymethyl cellulose | 0.1-2 grams |
| sodium alginate | 0.1-4 grams |
| polyvinyl alcohol | 0.1-10 grams |
| sodium acetate | 0.5-2 grams |
| coal-based activated carbon powder | 0.1-10 grams |
| diatomaceous earth powder | 1-10 gram, | the balance being water.

2. A process for manufacturing an artificial biomembrane, the process comprising:
(a) dissolving sodium alginate, polyvinyl alcohol and sodium carboxymethyl cellulose in water, and heating to 85-90° C. until sodium alginate, polyvinyl alcohol and sodium carboxymethyl cellulose are dissolved completely to form a glue liquid, and cooling said glue liquid to between 20 and 25° C.;
(b) mixing coal-based activated carbon powder, diatomaceous earth powder, sodium acetate and a concentrated suspension of microbial cells together to form a mixture, wherein said coal-based activated carbon powder is between 100 and 200 mesh, said diatomaceous earth powder is between 100 and 180 mesh, said concentrated suspension of microbial cells comprises a single strain, or comprises two or three kinds of microbial strains and has a concentration of about $1 \times 10^9 - 1 \times 10^{10}$ cells/ml;
(c) adding the mixture obtained in (b) to the glue liquid obtained in (a), then adding water and mixing uniformly to obtain a final glue liquid; wherein the final glue liquid comprises per 100 ml: between $10^{11}$ and $10^{12}$ of microbial cells, between 0.1 and 2 grams of sodium carboxymethyl cellulose, between 0.1 and 4 grams of sodium alginate, between 0.1 and 10 grams of polyvinyl alcohol, between 0.5 and 2 grams of sodium acetate, between 0.1 and 10 grams of coal-based activated carbon powder, between 0.5 and 10 grams of diatomaceous earth powder, the balance being water;
(d) utilizing a spray device to spray the final glue liquid obtained in (c) to form fogdrops and microcapsules, allowing the fogdrops and the microcapsules to land freely on powder beds or fluidized beds, whereby the fogdrops and the microcapsules are immobilized to form an artificial membrane, wherein the powder beds or the fluidized beds comprise silicon dioxide powder, boric acid powder and gypsum powder, and the weight ratio of the silicon dioxide powder, the boric acid powder and the gypsum powder is 1-6:0.1-3:0.1-3.

3. A process for manufacturing an artificial biomembrane, the process comprising:
(a) dissolving sodium alginate, polyvinyl alcohol and sodium carboxymethyl cellulose in water, and heating to 85-90° C. until sodium alginate, polyvinyl alcohol and sodium carboxymethyl cellulose are dissolved completely to form a glue liquid, and cooling said glue liquid to between 20 and 25° C.;
(b) mixing coal-based activated carbon powder, diatomaceous earth powder, sodium acetate and a concentrated suspension of microbial cells together to form a mixture, wherein said coal-based activated carbon powder is between 100 and 200 mesh, said diatomaceous earth powder is between 100 and 180 mesh, said concentrated suspension of microbial cells a comprises single strain, or comprises two or three kinds of microbial strains and has a concentration of about $1 \times 10^9 - 1 \times 10^{10}$ cells/ml;
(c) adding the mixture obtained in (b) to the glue liquid obtained in (a), adding water to required volume and mixing uniformly to obtain a final glue liquid; wherein per 100 ml of the final glue liquid comprising: between $10^{11}$ and $10^{12}$ of microbial cells, between 0.1 and 2 grams of sodium carboxymethyl cellulose, between 0.1 and 4 grams of sodium alginate, between 0.1 and 10 grams of polyvinyl alcohol, between 0.5 and 2 grams of sodium acetate, between 0.1 and 10 grams of coal-based activated carbon powder, between 0.5 and 10 grams of diatomaceous earth powder, the balance being water;
(d) putting the final glue liquid obtained in (c) in a container containing 500 sharp hole pipes in the bottom, dripping the final glue liquid freely or under pressure through the sharp hole pipes onto powder beds or fluidized beds for to form an artificial membrane immobilization, wherein the powder beds or the fluidized beds comprise silicon dioxide powder, boric acid powder and gypsum powder, and the weight ratio of the silicon dioxide powder, the boric acid powder and the gypsum powder is 1-6:0.1-3:0.1-3; and using a vibration screen to separate silicon dioxide powder, boric acid powder and gypsum powder from the artificial biomembrane.

4. An artificial biomembrane manufactured according to the process of claim 2.

5. An artificial biomembrane manufactured according to the process of claim 3.

6. A process for manufacturing an artificial biomembrane, the process comprising:
(a) dissolving sodium alginate, polyvinyl alcohol and sodium carboxymethyl cellulose in water, and heating to 85-90° C. until sodium alginate, polyvinyl alcohol and sodium carboxymethyl cellulose are dissolved completely to form a glue liquid, and cooling said glue liquid to between 20 and 25° C.;

(b) mixing coal-based activated carbon powder, diatomaceous earth powder, sodium acetate and a concentrated suspension of microbial cells together to form a mixture, wherein said coal-based activated carbon powder is between 100 and 200 mesh, said diatomaceous earth powder is between 100 and 180 mesh, said concentrated suspension of microbial cells comprises a single strain, or comprises two or three kinds of microbial strains and has a concentration of about $1\times10^9$-$1\times10^{10}$ cells/ml;

(c) adding the mixture obtained in (b) to the glue liquid obtained in (a), then adding water and mixing uniformly to obtain a final glue liquid;

(d) utilizing a spray device to spray the final glue liquid obtained in (c) to form fogdrops and microcapsules, allowing the fogdrops and the microcapsules to land freely on powder beds or fluidized beds, whereby the fogdrops and the microcapsules are immobilized to form an artificial membrane, wherein the powder beds or the fluidized beds comprise silicon dioxide powder, boric acid powder and gypsum powder, and the weight ratio of the silicon dioxide powder, the boric acid powder and the gypsum powder is 1-6:0.1-3:0.1-3; or putting the final glue liquid obtained in (c) into a container containing sharp hole pipes at the bottom, dripping the final glue liquid freely or under pressure through the sharp hole pipes onto powder beds or fluidized beds for to form an artificial membrane immobilization, wherein the powder beds or the fluidized beds comprise silicon dioxide powder, boric acid powder and gypsum powder, and the weight ratio of the silicon dioxide powder, the boric acid powder and the gypsum powder is 1-6:0.1-3:0.1-3; and using a vibration screen to separate silicon dioxide powder, boric acid powder and gypsum powder from the artificial membrane.

7. An artificial biomembrane manufactured according to the process of claim 6.

* * * * *